United States Patent [19]

Kreiskorte

[11] Patent Number: 4,682,498
[45] Date of Patent: Jul. 28, 1987

[54] SURFACE TESTING APPARATUS

[75] Inventor: Ing. H. Kreiskorte, Dortmund, Fed. Rep. of Germany

[73] Assignee: Thyssen Industrie AG, Essen, Fed. Rep. of Germany

[21] Appl. No.: 877,846

[22] Filed: Jun. 24, 1986

[30] Foreign Application Priority Data

Jul. 5, 1985 [DE] Fed. Rep. of Germany ....... 3524106

[51] Int. Cl.$^4$ .......................................... G01N 29/00
[52] U.S. Cl. ....................................... 73/618; 73/633;
73/634; 73/159
[58] Field of Search .................. 73/618, 633, 634, 159

[56] References Cited

U.S. PATENT DOCUMENTS 4,065,976 1/1978 Taenzer et al. .................. 73/633
4,258,319 3/1981 Shimada et al. .................. 324/226
4,562,737 1/1986 Davies .............................. 73/633

FOREIGN PATENT DOCUMENTS

| 923747 | 2/1955 | Fed. Rep. of Germany . |
| 2044331 | 3/1971 | Fed. Rep. of Germany . |
| 2458606 | 3/1979 | Fed. Rep. of Germany . |
| 2746618 | 4/1979 | Fed. Rep. of Germany . |
| 3324444 | 1/1984 | Fed. Rep. of Germany . |
| 3411854 | 10/1984 | Fed. Rep. of Germany . |
| 2084735 | 4/1982 | Switzerland . |
| 711237 | 6/1954 | United Kingdom . |

Primary Examiner—Anthony V. Ciarlante

[57] ABSTRACT

The invention relates to a surface testing apparatus in which sensors are driven with a reciprocating movement above the surface being tested. To minimize the forces which are required for the driving of the sensors, a vibratory system is provided for this movement, which is driven by an exciter system at or close to its natural frequency.

10 Claims, 10 Drawing Figures

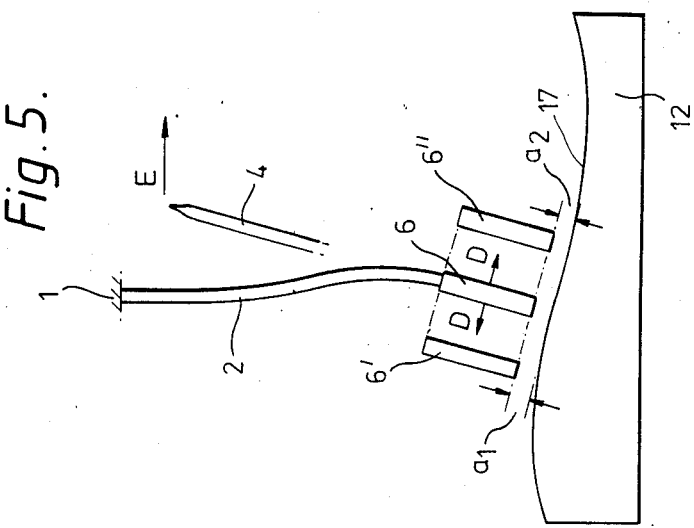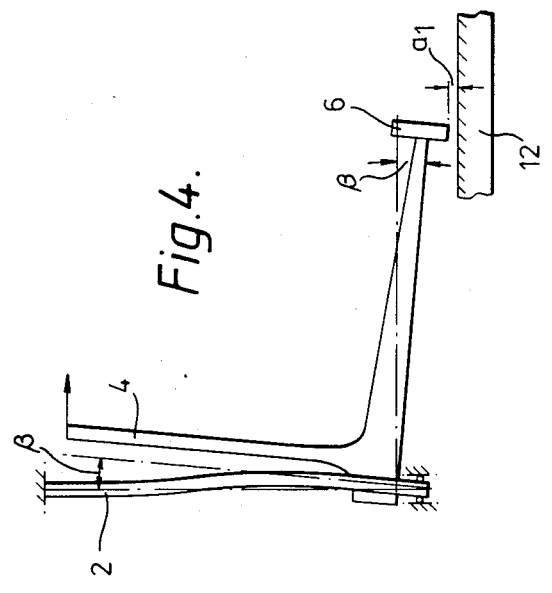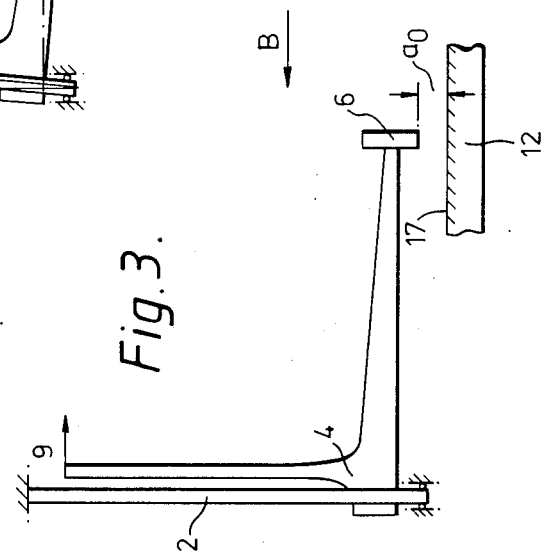

SURFACE TESTING APPARATUS

BACKGROUND OF THE INVENTION

In order to detect and locate cracks and other surface defects in slabs for rolling steel flats, suitable sensors are used. These sensors (based on eddy currents, for example, according to DE-OS No. 20 44 331) must usually be disposed closely (e.g., 4 mm) above the surface and they have only a narrow effective range. To be able to scan larger surface areas with a sensor, the sensor can be moved back and forth within a certain range over the slab emerging continuously from a strand casting apparatus. This movement can be performed, for example, by a crank drive (DE-OS 27 46 618) which makes a carriage running on guides shift back and forth.

For the scanning pattern to be narrow enough, the reciprocating movement of the sensors must be fast, and the mass forces which this produces increase as the square of the scanning frequency and can become very great.

It is, therefore, an object of this invention to provide a surface testing apparatus by means of which the sensors can be moved back and forth over the surface with a high scanning frequency.

A further object is to minimize the forces which are required for the movement of the sensors.

A further object is to provide a surface testing apparatus with a vibratory system for moving the sensors and for operating the vibratory system at or close to its natural frequency.

According to the invention it is proposed, for moving the sensors back and forth, to employ an oscillating system which is driven by means of an exciter system at or close to its natural frequency. Since the distance of the sensors from the surface being examined must be kept within close tolerances, it is additionally proposed to control the height and lateral inclination of the sensors by the deformation of resilient elements or to hold the sensors at a constant distance from the surface under examination by means of biased pneumatic or hydrostatic thrust bearings.

Additional advantageous features of the invention will be found in the subordinate claims.

Embodiments of the invention will be seen in the drawings.

SUMMARY OF THE DRAWINGS

FIG. 3 is a schematic representation of the test apparatus, FIG. 4 is a schematic representation of the test apparatus with height adjustment, FIG. 5 is a schematic representation of the test apparatus with lateral inclination.

Figure 1:
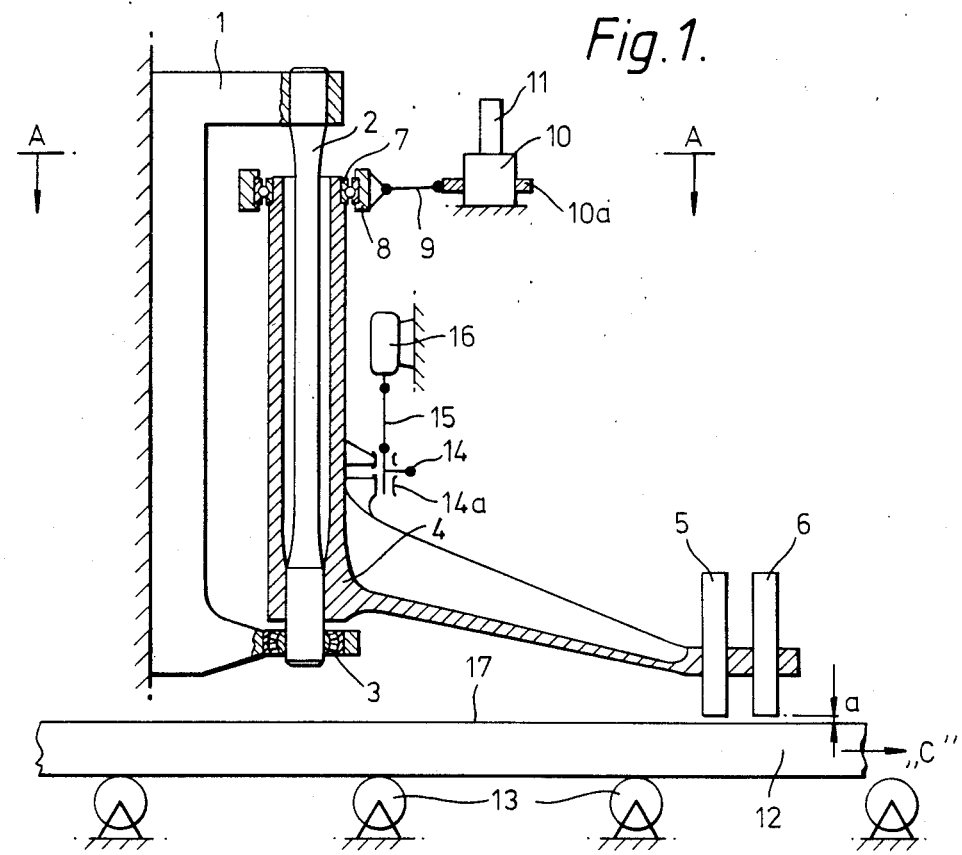
FIG. 1 is a side view of a test apparatus based on a torsional vibration system.

A test apparatus based on a torsional vibration system is represented in a side view in FIG. 1. In this system a torsion bar 2 is fixedly held at its upper end in a foundation frame. The bottom end of the torsion bar 2 is journaled in the foundation frame 1 by means of a bearing 3. Also, an oscillating arm 4 is affixed to the bottom end of the torsion bar 2. The oscillating arm 4 in turn carries a distance sensor 5 and a crack sensor 6. The distance and crack sensors, operating preferably by induction or with eddy currents, are known in themselves (DE-OS No. 20 44 331, 27 46 618, 33 24 444, or U.S. Pat. No. 4,258,319), and therefore need no further explanation. At the upper end of the oscillating arm a bearing 7 is disposed in a freely movable bearing case 8. The bearing case 8 can be moved through a preferably flexible connector 9 by means of a thruster or displacement means 10. The thruster 10 is driven by a motor 11 and contains, for example, a pinion or the like (not shown) driven by the motor 11 and driving a toothed rack 10a, a threaded spindle or the like which is connected to the connector 9. Parts 9, 10 and 11 form a first adjusting means for the oscillating arm.

Underneath the test apparatus there is disposed a workpiece 12 which is to be tested, which is continuously advanced in the direction of the arrow C over rolls 13.

The test apparatus is operated in resonance by means of a centrifugal force exciter system. This contains a centrifugal force exciter 14, for example in the form of an excentric, which is journaled in a bearing 14a fastened to the oscillating arm 4 and is fastened to a flexible shaft or universal shaft 15 driven by a variable-speed motor 16.

In the operation of the test apparatus, the oscillating arm 4 with the sensors 5 and 6 is moved back and forth at the distance "a" above a surface 17 of the workpiece 12 being tested. If at the same time the workpiece 12 is continuously moved in the direction of an arrow "C," the surface 17 being tested is scanned linearly. The torsion bar 2, the oscillating arm 4 and the sensors 5 and 6 form a mechanical oscillatory system which is driven by the exciter system 14, 14a, 15 and 16 at its resonant frequency or at a frequency close to same.

Figure 2:
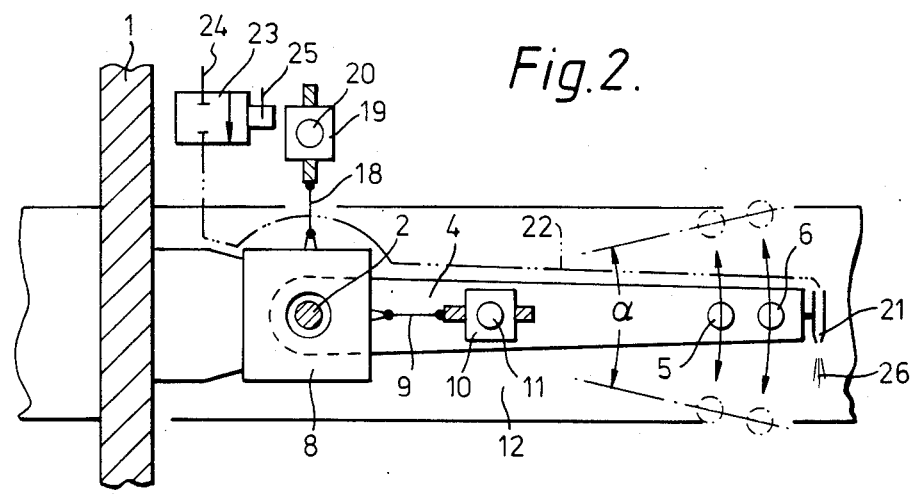
FIG. 2 is a section along line A—A in FIG. 1, but with a different exciter.

FIG. 2 shows a test apparatus corresponding to the section A—A of FIG. 1. Instead of the centrifugal force exciter system 14, 14a, 15 and 16, a different exciter system is used here for the excitation of the oscillating system vibrating at resonance or close to resonance.

Air fed through an air duct 22 and a valve 23 is discharged through an air nozzle 21, the air being delivered to the valve 23 through a compressed-air line 24. If the valve 23 is opened and closed by an electrical signal through an electrical lead 25 at the natural frequency of the vibrating system, an air stream 26 is discharged from the air nozzle 21 in time with the switching frequency, producing a recoil or reaction pulse at the free end of the air nozzle 21 which is connected to the oscillating arm. This recoil pulse suffices to produce an amplitude of 300 mm at the sensors 5 and 6 in the special vibratory system to be described hereinbelow.

If a diameter of 25 mm and a length of 600 mm is selected for the torsion bar 2 made of steel, the result will be a torsion spring number (directional torque) of, for example, $c = 5.16 \times 10^3$ Nm. The mass moment of inertia of the oscillating system about the axis of the torsion bar is determined substantially by the mass of the sensors 5 and 6. To this is added the mass moment of inertia of the oscillating arm 4. Assuming a reduced mass, with reference to an oscillation radius of one meter, of 5 kg with respect to this radius, the result is a mass moment of inertia of $\theta = 5$ Nms².

On the basis of the torsion spring number c and the mass moment of inertia, the natural frequency is calculated as:

$$f_0 = \tfrac{1}{2}\pi \sqrt{\tfrac{c}{\theta}} = 5.1 \text{ Hz.}$$

If such a vibrating system is excited in the vicinity of its natural frequency, the result will be a considerable resonant amplification (resonance rise), i.e., the force required for the excitation and driving of the vibrating system is substantially less than the force necessary for the movement of the masses.

If the vibratory system described above with the natural frequency of $f_O = 5.1$ Hz is driven at a frequency of 5 Hz, the resonant amplification, disregarding damping, will be $$V = \frac{1}{1 - (f/f_o)^2} = 25.7.$$

For the driving of the test system, therefore, a force will be required which amounts to only about 1/25 of the force necessary for moving the masses back and forth.

According to FIG. 2, a second adjusting means 18, 19 and 20 for the oscillating arm 4 is provided in addition to the first adjusting system 9, 10 and 11 described in FIG. 1, whereby the movable bearing case 8 can be shifted laterally and which, like the first adjusting means, has a preferably flexible coupling member 18, a lifting mechanism or displacing means 19 and a motor 20.

Since the distance "a" must be preserved as accurately as possible, the height of the sensors 5 and 6 has to be adjusted if the level of the surface of the workpiece undergoes any fluctuations. If the distance "a" must be reduced, the bearing case 8 is drawn rightward by means of the motor 11, thruster 10 and the coupling member 9, as will be further described below in conjunction with FIGS. 3 to 5, in which the adjustment is represented exaggeratedly large and diagrammatically. The oscillating arm 4 is thereby tipped to the right slightly about the bottom bearing 3, which for example is in the form of a self-aligning roller bearing or the like, and permits slight rocking of the torsion bar 2. At the same time the torsion bar is flexed.

The arrangement in FIG. 3 shows the starting state, in which the sensor 6 is at a distance "$a_0$" from the surface 17 of the workpiece 12.

If now, in accordance with FIG. 4, the upper bearing case 8 of the oscillating arm 4 is shifted to the right, the bottom end of the torsion bar 2 tilts by the angle $\beta$. The oscillating arm 4 is bent downwardly toward the workpiece 12 by the same angle, and the distance "$a_0$" diminishes to "$a_1$".

If the surface of the workpiece 12 can differ not only in level but also in lateral inclination, it is proposed also to flex or bend the torsion bar 2 also transversely.

FIG. 5 shows the test apparatus in the direction of the arrow "B" in FIG. 3. The cross section of the workpiece 12, which extends forward continuously from the plane of the drawing, has the contour represented in the drawing, for example. In order for the sensor 6 vibrating transversely in the direction of the arrows "D" to have substantially the same distance "a" from the surface 17, the vibratory system must be displaced in the direction of the arrow "E." The sensor 6 then moves in its oscillatory movement to the end positions 6' and 6". This causes the torsion bar 2 to be flexed transversely in addition to its torsional movement. The elements necessary for this purpose (FIG. 2) are the coupling member 18, the thruster 19 and the motor 20 of the second adjusting means as well as the bearing case 8, the bearing 7 being preferably also in the form of a self-adjusting roller bearing or the like.

The vertical adjustment of the distance "a" can be performed by means of a regulating circuit if the contour of the workpiece varies, the actual distance from the surface being determined by the space sensor 5. The actual distance that is measured is compared with the specified distance. If there are differences between the actual distance and the specified distance, a correction is made by means of the first adjusting means.

Accordingly, it is also possible to correct the lateral inclination. For this purpose the distances "$a_1$" and "$a_2$" are determined at the end positions of the oscillating sensors. If "$a_1$" and "$a_2$" are not equal, a corresponding correction is made through a closed control circuit with the second adjusting means 18, 19, 20.

In the embodiment according to FIG. 1, a centrifugal force exciter 14 is used to excite the vibratory system. The centrifugal force exciter 14 is driven, for example, by a controllable motor 16 through a universal shaft 15. In such a system it is desirable, to operate in the ascending limb of the resonance curve. The amplitude of vibration can be measured by means of strain gauges disposed on the torsion bar 2 and can be kept constant by means of a regulating circuit.

The vibratory system, however, can be excited by other means, such as, for example, a spring force exciter or a pulsing air jet system (e.g., FIG. 2).

Figure 6:
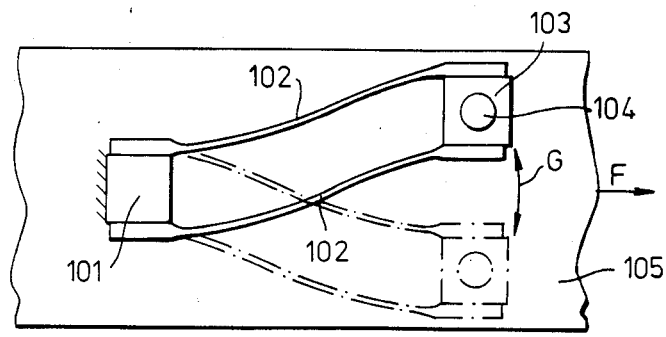
FIG. 6 is a top plan view of a testing apparatus on the basis of a leaf spring vibration system.
Figure 7:
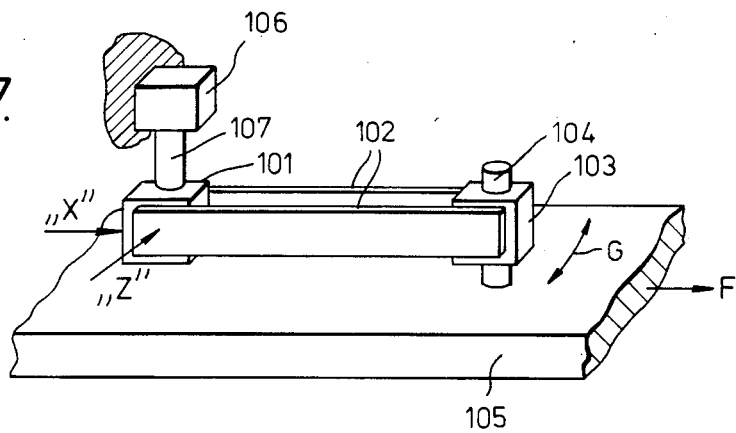
FIG. 7 is a perspective view of the test apparatus according to FIG. 6.

Another example of a vibratory system is represented in FIGS. 6 and 7. Leaf springs 102 are fastened to a post 101 and in turn bear a holder 103 for a sensor 104. A workpiece 105 moves continually in the direction of the arrow F. The exciter system causing the system to vibrate and flex in the direction of the arrow "G" is not shown in the drawing, and can be constructed, for example, as in FIGS. 1 and 2.

In FIG. 7 is shown how the height and lateral inclination can be adjusted. If a force is applied to the vibratory system in the direction of the arrow "X" a resiliently flexible member 107 gripped between a fixed block 106 and the post 101 flexes slightly and the sensor 104 is lifted slightly upward. If force is applied in the direction of the arrow "Z" the system is tilted, so that the sensor 104 can follow a correspondingly inclined surface.

Figure 8:
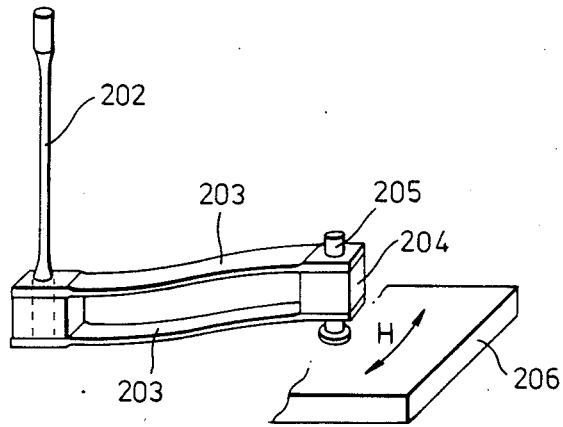
FIG. 8 is a torsional vibration system with a resilient height bias for a contact source bearing.
Figure 9:
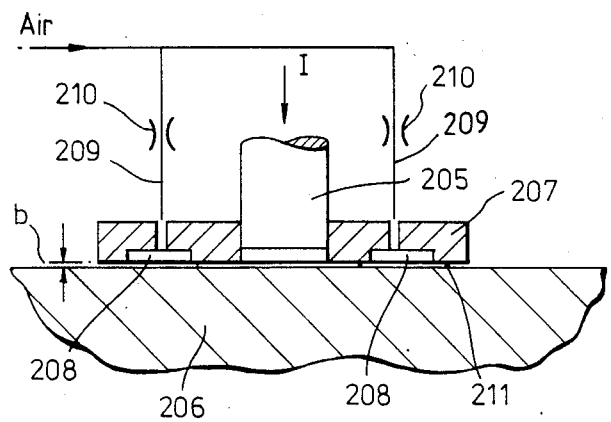
FIG. 9 is a pneumatic contact source bearing for the sensor.

FIGS. 8 and 9 show an arrangement in which a sensor 205 is kept at its distance from the surface being tested by means of a spring-biased support.

In FIG. 8, a torsion bar 202 and the masses oscillating in the direction of the arrow "H" again form a vibratory system. The oscillating arm 4 (FIG. 1) consists in this embodiment of a pair of leaf springs 203. This pair of leaf springs bears a holder 204 with the sensor 205. The leaf springs 203 are so arranged that they are flexed slightly upward and press the sensor 205 against a workpiece 206.

Since this arrangement would produce friction between the sensor 205 and the surface of the workpiece 206, a pneumatic thrust bearing is provided to create an air cushion for the maintenance of a space "b" between the sensor 205 and the workpiece 206 (FIG. 9) against the thrust of the leaf springs 203. The sensor 205 thus floats on this air cushion above the surface being tested and can move in a largely friction-free manner.

FIG. 9 shows a preferred embodiment of a pneumatic thrust bearing. A supporting disk 207 is connected with the sensor 205. In this supporting disk 207 a plurality of air pockets 208 are distributed around its circumference. Air is blown into each of these air pockets 208 through ducts 209 and, if desired, throttles 210. The air lifts the supporting disk 207 against the force "I" which is produced by the leaf springs 203. This creates a gap "b" through which the air escapes outwardly. The throttles 210 and the gap "b" between the supporting disk 207 and the surface being tested thus form a kind of bridge circuit which automatically regulates the pressure in the pockets 208. Instead of the throttle 210 the air ducts 209 can be made so thin that they provide the desired throttling action.

To enable to sensor to adapt to any inclination of the surface being tested, it is desirable to introduce the force acting in the direction of the arrow "I" through a Cardan's suspension.

The bias for the thrust bearing can also be provided by magnets. This bias then replaces the force "I" which is applied by the leaf springs.

Figure 10:
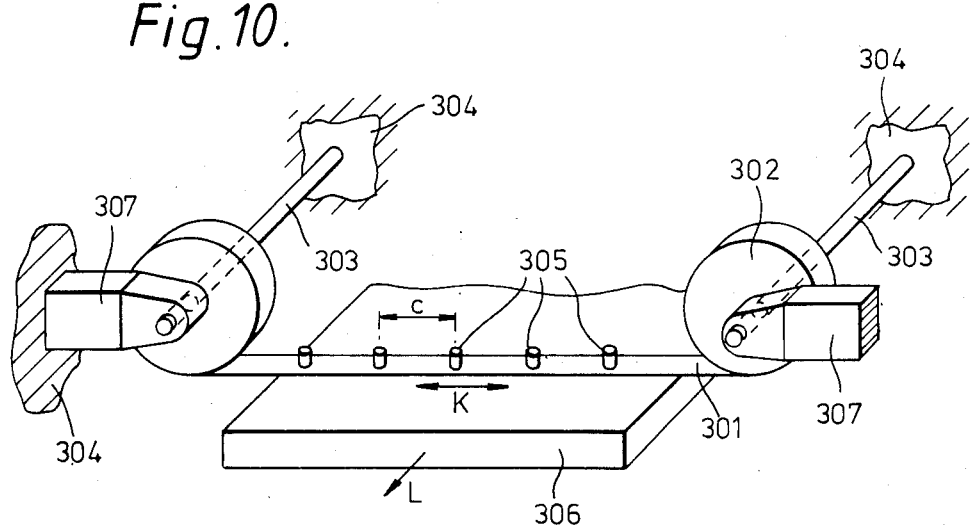
FIG. 10 is a vibratory system in which a biased belt with sensors oscillates over the surface.

In FIG. 10 is shown a vibratory system in which a biased steel band 301 is stretched around pulleys 302. The pulleys 302 are joined to a machine housing 304 by torsion bars 303 and journaled in bearings 307. The result is a vibratory system in which the two pulleys 302 and the torsion bars 303 perform rotary vibrations of equal sense. In these rotary vibrations the steel band 101 is moved back and forth in the direction of the arrow "K". The bias is produced in the steel band 301 by the fact that at least one of the torsion bars 303 is twisted by a certain angular amount when the steel band is in the rest position.

If sensors 305 are disposed successively in the direction of the oscillation of the steel band 301 with the spacing "c," in one vibratory movement of the steel band 301 with a double amplitude that is slightly greater than the spacing "c," the entire width of the workpiece 306 is scanned. The test apparatus according to FIG. 10 is suitable especially for the scanning of comparatively wide workpieces 306, e.g., steel slabs about 2 meters wide which are moving perpendicular to the direction of oscillation.

If the workpiece is additionally moved in the direction of the arrow "L" the entire surface is examined linearly for cracks or surface flaws.

The invention brings with it the important advantage that only comparatively low forces are required in order to excite the vibratory system and sustain its vibration, if the oscillation is performed at the resonant frequency or at a frequency close to resonance. There is the additional advantage that, for the purpose of varying the distance between the sensors and the workpiece, the torsion bars (e.g., FIGS. 1 to 5) or springs (e.g., FIGS. 6 to 9) are themselves flexed or are suspended on easily flexible elements, so that no additional bearings or masses are required for the adjustment. In this manner, vibration frequencies of at least 5 Hz can easily be produced, which are necessary in order to scan a workpiece 12 moving at a velocity of, e.g., 20 mm/sec, five times per second at twice the vibration amplitude, e.g., 4 millimeters, without leaving any parts of its surface untested.

Although the invention has been described and illustrated with respect to preferred embodiments thereof, it is to be understood that it is not to be so limited since changes and modifications may be made therein which are within the full intended scope of the invention.

I claim:

1. A surface testing apparatus comprising: at least one sensor (5, 6, 104, 205, 305) for testing a surface (17), carrier means (4, 103, 204, 301) for carrying said sensor, means for reciprocatingly moving said carrier such that said sensor is reciprocatingly moved over said surface, said moving means being constructed as a vibratory system having a natural frequency and including said carrier, and an exciter means (14, 14a, 15 or 21, 22, 23, 24, 25, respectively) for operating said vibratory system at or in the neighborhood of its natural frequency such that said sensor is moved over said surface with said natural frequency or with a frequency in the neighborhood thereof.

2. Surface testing apparatus according to claim 1, characterized in that the vibratory system is a torsion vibration system having at least one torsion bar (2, 202, 303), said carrier means being an oscillating arm (4, 203) connected to said torsion bar.

3. Surface testing apparatus according to claim 2, characterized in that said carrier means (204) is coupled to said torsion bar (202) by means of resilient means (203) wheels press said sensor (205) against the surface to be tested.

4. Surface testing apparatus according to claim 3, characterized by fluid thrust bearings (207, 208, 209, 210) for making said sensor (205) float at a slight distance above the surface to be tested.

5. Surface testing apparatus according to claim 1, characterized in that the vibratory system is composed of at least one leaf spring (102), one part thereof being coupled to a fixed portion of said apparatus and another part thereof carrying said sensor.

6. Surface testing apparatus according to claim 1, characterized in that said vibratory system is a torsion vibration system (302, 303) and that said carrier is a band (301) reciprocatingly moved by said torsion vibration system.

7. Surface testing apparatus according to claim 1, characterized in that said exciter means is a recoil-producing system comprising an air nozzle (21), a line (22,24) being connected to said air nozzle (21) and feeding compressed air thereto, and a valve (23) being disposed in said line, which valve may be turned on and off at the natural frequency of the vibratory system or at a frequency in the vicinity thereof.

8. Surface testing apparatus according to claim 1, wherein said carrier is designed such that said sensor is carried above said surface at a distance thereto.

9. Surface testing apparatus according to claim 1, characterized by a first adjustment means (9,10,11) for varying the distance between the sensor (5, 6, 104, 205, 305) and the workpiece (12, 105, 206, 306).

10. Surface testing apparatus according to claim 1, characterized by a second adjustment means (18, 19, 20) for varying the lateral inclination of the sensor (5, 6, 105, 205, 305).

* * * * *